(12) United States Patent
Banik et al.

(10) Patent No.: US 8,827,956 B2
(45) Date of Patent: Sep. 9, 2014

(54) SYRINGE HOUSING TO FACILITATE MEDICATION INJECTION

(75) Inventors: Robert Banik, Long Valley, NJ (US); James Bates, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 441 days.

(21) Appl. No.: 13/127,454

(22) PCT Filed: Nov. 6, 2009

(86) PCT No.: PCT/US2009/006013
§ 371 (c)(1),
(2), (4) Date: Jun. 20, 2011

(87) PCT Pub. No.: WO2010/053570
PCT Pub. Date: May 14, 2010

(65) Prior Publication Data
US 2011/0251587 A1    Oct. 13, 2011

Related U.S. Application Data

(60) Provisional application No. 61/193,235, filed on Nov. 7, 2008.

(51) Int. Cl.
*A61M 5/00* (2006.01)
(52) U.S. Cl.
USPC .......................................... 604/117; 604/115
(58) Field of Classification Search
CPC ................................ A61M 5/46; A61M 5/42
USPC ......... 604/506, 511, 513, 115, 177, 181, 187, 604/218, 117, 272
See application file for complete search history.

(56) References Cited

U.S. PATENT DOCUMENTS

| 4,664,128 | A | * | 5/1987 | Lee ................................ 600/566 |
| 5,222,945 | A | * | 6/1993 | Basnight ....................... 604/110 |
| 6,494,865 | B1 | | 12/2002 | Alchas |
| 6,569,123 | B2 | | 5/2003 | Alchas et al. |
| 6,569,143 | B2 | | 5/2003 | Alchas et al. |
| 6,689,118 | B2 | | 2/2004 | Alchas et al. |
| 6,776,776 | B2 | | 8/2004 | Alchas et al. |

(Continued)

FOREIGN PATENT DOCUMENTS

| JP | 1-268563 | 10/1989 |
| JP | 7-504346 | 5/1995 |

(Continued)

OTHER PUBLICATIONS

Japanese Office Action issued in JP Patent Application No. 2011-535561 dated Sep. 10, 2013.

*Primary Examiner* — Emily Schmidt
(74) *Attorney, Agent, or Firm* — Roylance, Abrams, Berdo and Goodman, LLP

(57) ABSTRACT

A syringe (211) includes a syringe body (217) for receiving and administering a medicament. A needle (215) is received by the syringe body (217). A needle adjusting member (221) is movably disposed on the syringe body (217) between first and second positions. When the needle adjusting member (221) is in the first position, the needle (215) has a first length adapted to draw medicament into the syringe body (217). When the needle adjusting member (221) is in the second position, the needle (215) has a second length for injecting the medicament.

16 Claims, 9 Drawing Sheets

(56) References Cited

U.S. PATENT DOCUMENTS

| | | |
|---|---|---|
| 6,843,781 B2 | 1/2005 | Alchas et al. |
| 2007/0005017 A1* | 1/2007 | Alchas et al. ........... 604/117 |
| 2007/0016135 A1* | 1/2007 | Kanner et al. .......... 604/117 |
| 2007/0021719 A1* | 1/2007 | Alchas ..................... 604/117 |
| 2008/0045900 A1 | 2/2008 | Alchas |
| 2008/0132838 A1 | 6/2008 | Wyrick |

FOREIGN PATENT DOCUMENTS

| | | |
|---|---|---|
| JP | 2002-360693 | 12/2002 |
| JP | 2005-500871 | 1/2005 |
| JP | 2005-520602 | 7/2005 |
| JP | 3134719 | 8/2007 |
| JP | 2007-528274 | 10/2007 |
| JP | 2008-246190 | 10/2008 |

* cited by examiner

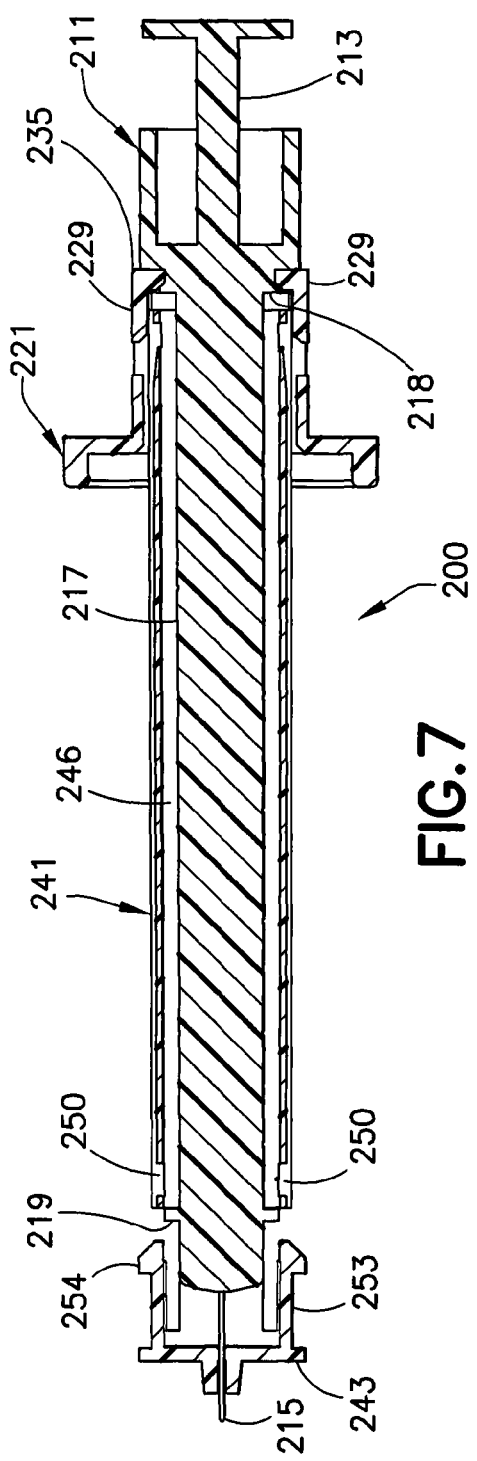
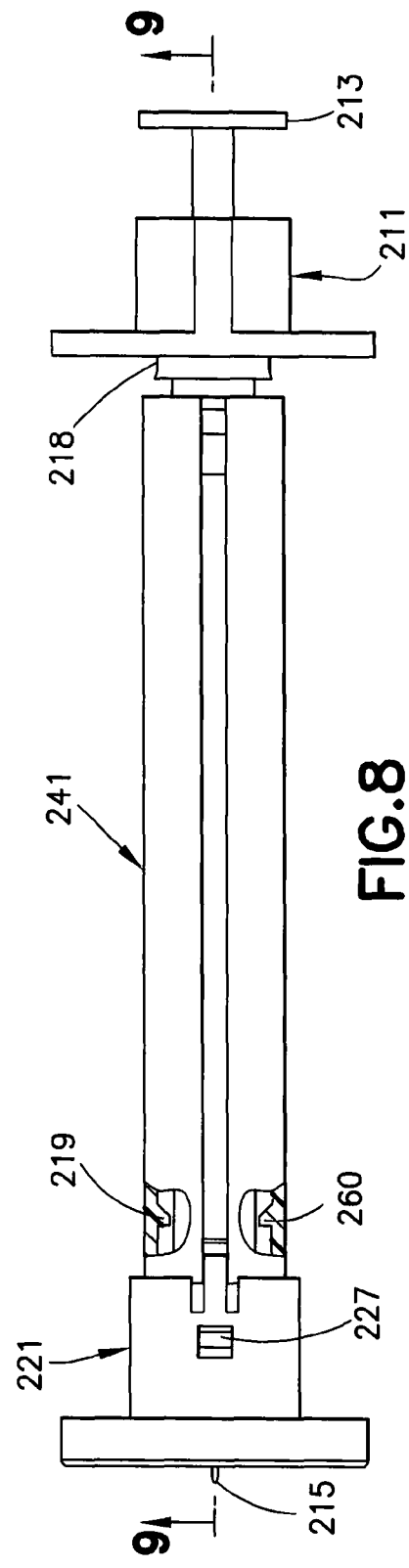

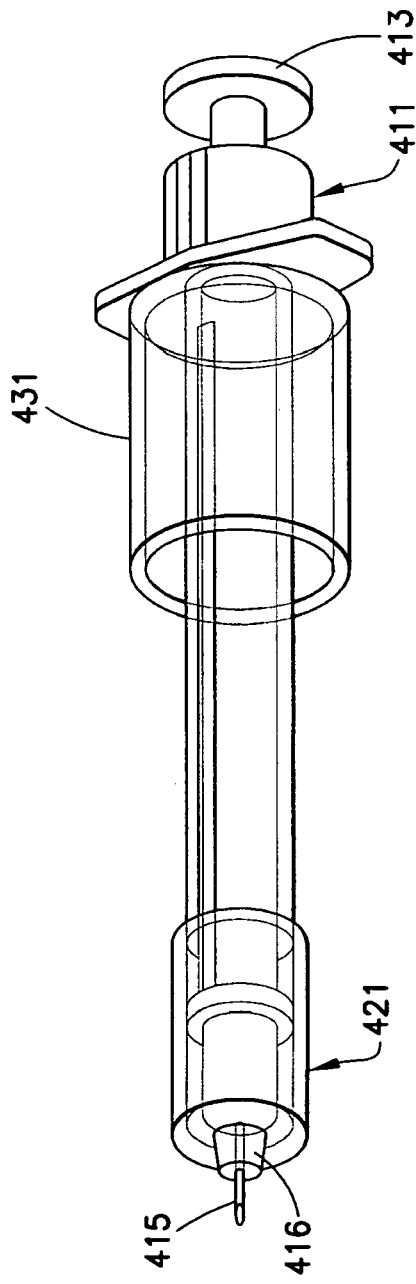
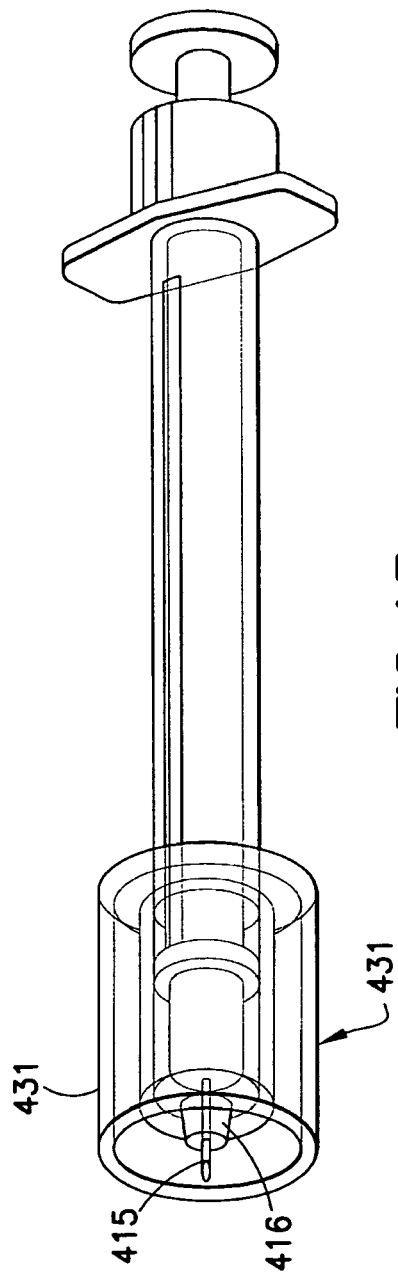
FIG. 14
FIG. 15

SYRINGE HOUSING TO FACILITATE MEDICATION INJECTION

CROSS REFERENCE TO RELATED APPLICATION

This application claims the benefit under 35 U.S.C. §119(e) of U.S. Provisional Application Ser. No. 61/193,235, filed Nov. 7, 2008, the entire disclosure of which is hereby incorporated by reference.

FIELD OF THE INVENTION

The present invention relates generally to a needle adjusting member for a syringe that facilitates a medication injection. More particularly, the present invention generally relates to a needle adjusting member adapted to be added to a standard syringe to facilitate a medication injection. Still more particularly, the present invention provides a needle adjusting member that shortens the effective needle length of a standard syringe, thereby facilitating a medication injection.

BACKGROUND OF THE INVENTION

An existing method to perform a medication injection delivers a drug substance into the subcutaneous region of the skin. It is possible that the same device may be used to delivery an intramuscular and a subcutaneous injection, with the health care provider controlling the depth of the injection.

Techniques and devices are known for administering an injection into the intradermal region of the skin. One method, commonly referred to as the Mantoux technique, uses a "standard" syringe, i.e., a syringe typically used to administer intramuscular or subcutaneous injections. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

As advances in understanding the delivery of drug proceeds, the use of intradermal delivery systems is expected to increase. Use of a "standard" length needle to deliver a drug substance intradermally has its shortcomings, as noted above. It is not possible to use a delivery device having a needle length suited for intradermal injection to aspirate a syringe with drug substance from a multi-use vial. Thus, there are shortcomings in the prior art that prevent administering an intradermal injection using a "standard" length needle and a multi-use vial. It would be advantageous to have a drug delivery device capable of accessing substances stored in multi-dose vials and delivering such substances into the intradermal region of the skin without encountering the shortcomings described above.

A conventional syringe 101 is shown in FIG. 1. The needle 103 is sufficiently long to aspirate a drug from a vial and deliver the drug to the subcutaneous region of the skin. However, a user would not be able to easily deliver the drug to the intradermal region of the skin, as discussed above. Thus, a need exists for a syringe adapted to facilitate an intradermal medication injection.

Another problem with providing syringes with needles having the appropriate length for intradermal delivery, which is approximately between 0.5-3 mm and preferably approximately between 1.5-2 mm, is that standard vials cannot be used because the septum thickness is thicker than the length of the needle. Therefore, such a syringe is prevented from being filled from a vial. Thus, a need exists for a syringe having a standard commercial needle length to be utilized for filling from a vial and also adapted to facilitate an intradermal medication injection.

Accordingly, a need exists for a needle adjusting member for a syringe that facilitates an intradermal medication injection.

SUMMARY OF THE INVENTION

In accordance with an aspect of the present invention, a needle adjusting member for a syringe is provided that facilitates a medication injection.

In accordance with another aspect of the present invention, a needle adjusting member allows a user to fill a standard syringe from a vial and to then inject the medicament, thereby providing a non-filled intradermal needle-based product.

In accordance with another aspect of the present invention, a syringe having a shorter needle length may be filled using a standard vial.

In accordance with another aspect of the present invention, a needle adjusting member is easily manufactured using a one-piece mold and adapted to fit on an existing syringe body.

In accordance with another aspect of the present invention, a wheal is allowed to form in the skin and expand to a larger size by pushing up on a movable platform, thereby reducing back pressure because the wheal is less restrained.

In accordance with another aspect of the present invention, the needle is fixed and allows the wheal to push back the back wall, thereby substantially preventing leaking compared to a floating needle design.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 7 is an elevational view in cross section taken along line 7-7 of FIG. 6;

FIG. 8 is an elevational view of the syringe assembly of FIG. 5;

FIG. 14 is a perspective view of the needle adjusting member disposed on the syringe of FIG. 13 in a first position; and FIG. 15 is a perspective view of the needle adjusting member disposed on the syringe of FIG. 13 in a second position.

Throughout the drawings, like reference numbers will be understood to refer to like parts, components and structures.

DETAILED DESCRIPTION OF THE EXEMPLARY EMBODIMENTS

Figure 1:
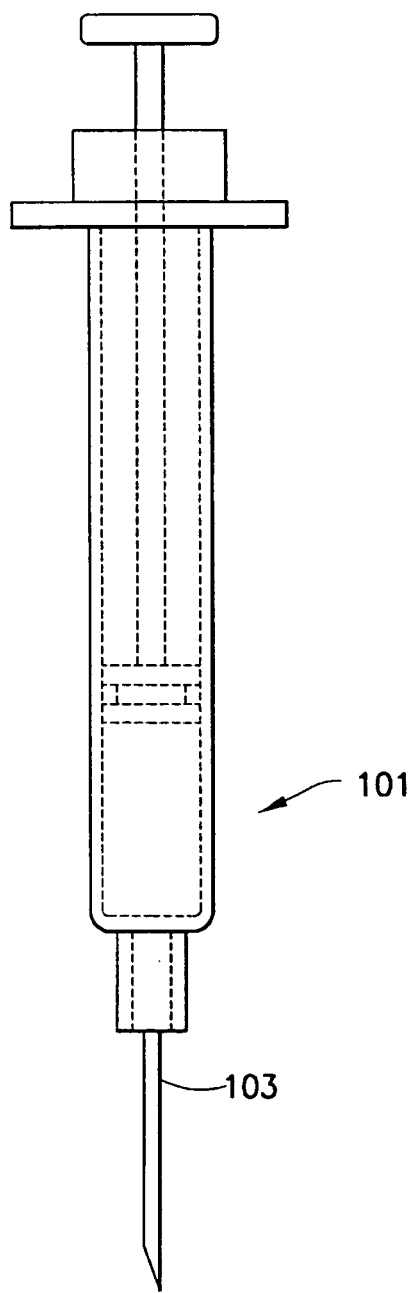
FIG. 1 is a front elevational view of a syringe.
Figure 2:
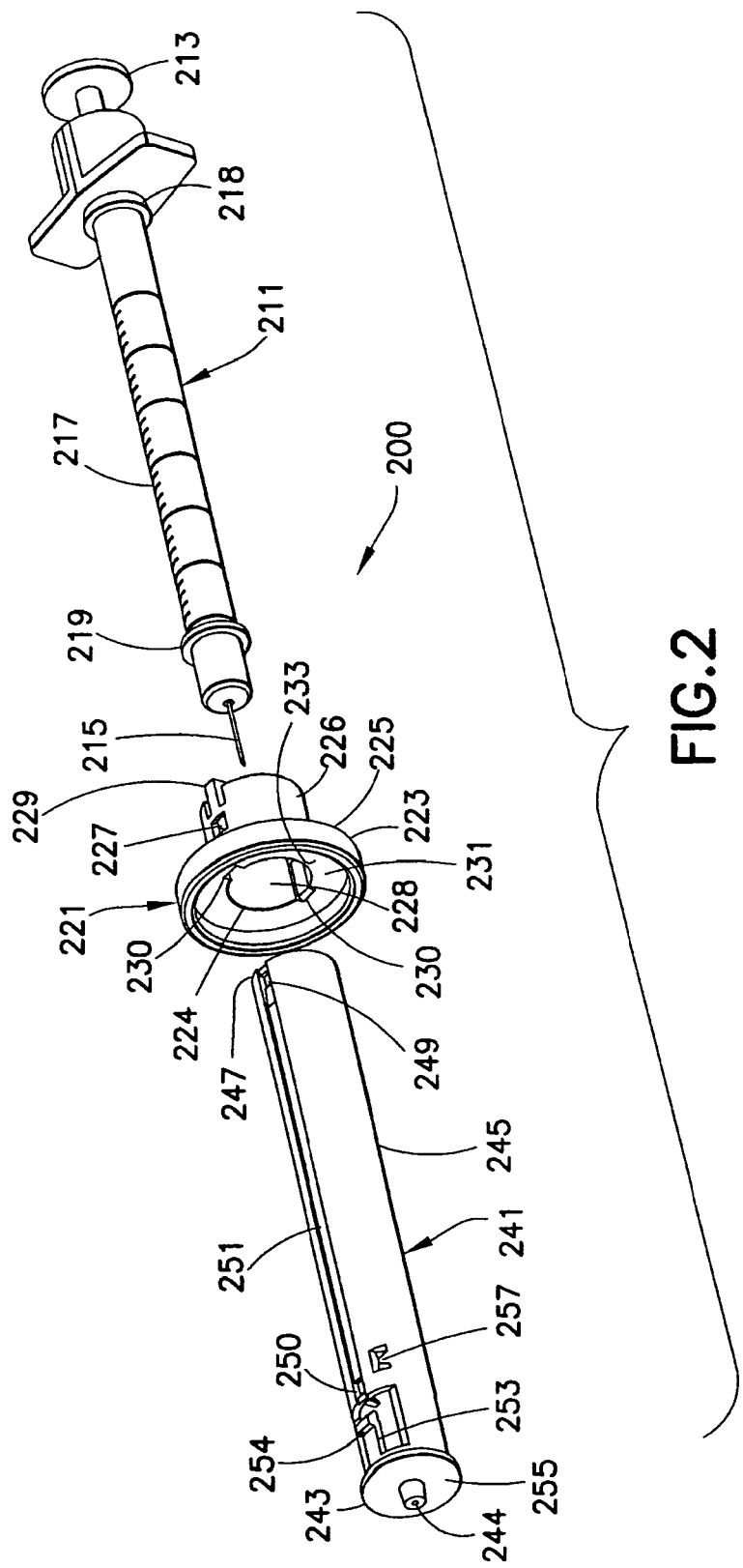
FIG. 2 is an exploded perspective view of a syringe and needle adjusting member according to a first exemplary embodiment of the present invention.

In a first exemplary embodiment of the present invention, as shown in FIGS. 2-9, a syringe-based intradermal needle assembly 200 is provided. A conventional insulin syringe 211 has a plunger 213 disposed at a first end and a needle 215 rigidly fixed at the second end. A flange 219 is disposed on the syringe body 217 proximal the needle 215, and a collar 218 is disposed on the syringe proximal the plunger 213. Medicament is drawn into and administered from a syringe body 217. A stopper is connected to the plunger 213 and moved through the syringe body 217 by the plunger. The syringe 211 has a longer exposed needle length that allows for normal vial-based syringe filling. After medicament filling and priming, the user slides the needle adjusting member toward the needle to shorten the effective length of the needle, thereby creating the stand-off and geometry necessary for a desired medication injection, such as an intradermal injection. The needle adjusting member 221 may create an effective short intradermal needle length, such as approximately 1.65 mm, although any suitable needle length may be created.

Figure 5:
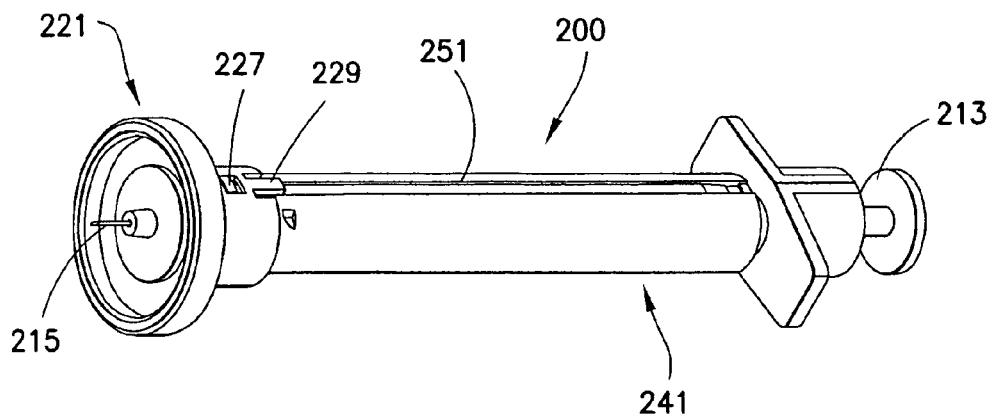
FIG. 5 is a perspective view of the needle adjusting member disposed on the syringe of FIG. 1 in a second position.
Figure 9:
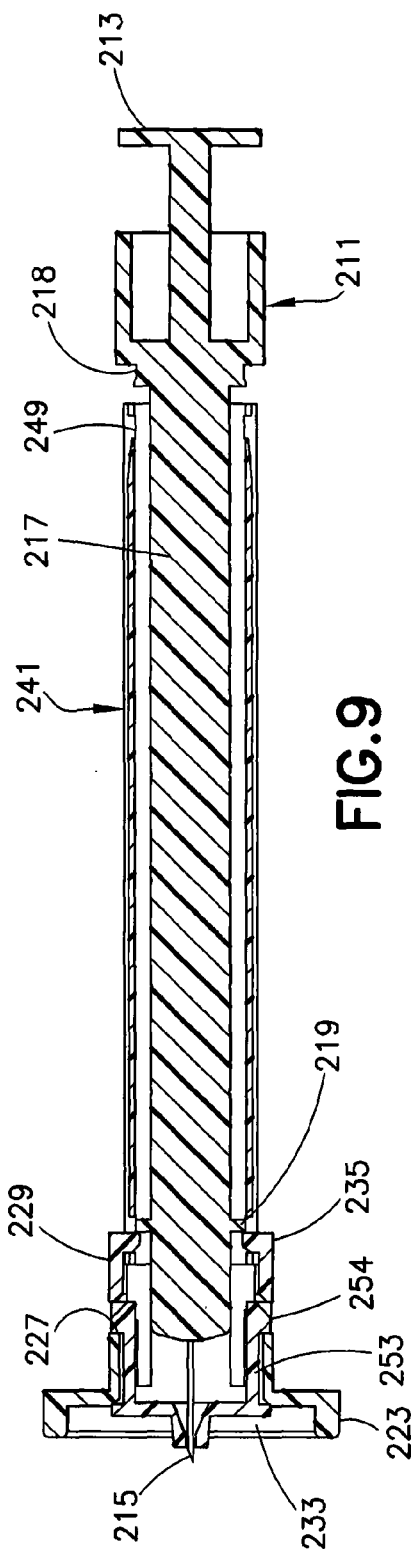
FIG. 9 is an elevational view in cross section taken along line 9-9 of FIG. 8.

The needle adjusting member 221 is movably disposed on the syringe body 217 between a first position (FIGS. 3, 6 and 7) and a second position (FIGS. 5, 8 and 9). When the needle adjusting member 221 is in the first position, the needle 215 has a first length adapted to draw medicament into the syringe body 217, such as from a vial. When the needle adjusting member 221 is in the second position, the needle 215 has a second length for intradermally injecting the medicament. The second length of the needle 215 is shorter than the first length of the needle.

The needle adjusting member 221 has a base 223 with an opening 224 therein. The base 223 forms a wide platform that stabilizes the syringe assembly 200 during an intradermal injection. A wall 226 extends upwardly from an upper surface 225 of the base 223. The wall 226 forms a passageway 228 aligned with the opening 224 in the base 223. A first opening 227 is formed in the wall 226, and a second opening is formed in the wall diametrically opposite the first opening. Diametrically opposed flexible arms 229 are formed in the wall 226 and extend axially upwardly (away from the base 223). Hooks 235 (FIGS. 7 and 9) are formed at the ends of the flexible arms 229. A pair of notches 230 extend radially outwardly from the opening 224 in the base 223 and are diametrically opposed. A space 233 is formed beneath the base 223 to provide an area for a skin bubble (wheal) to grow as a result of the injection.

Figure 3:
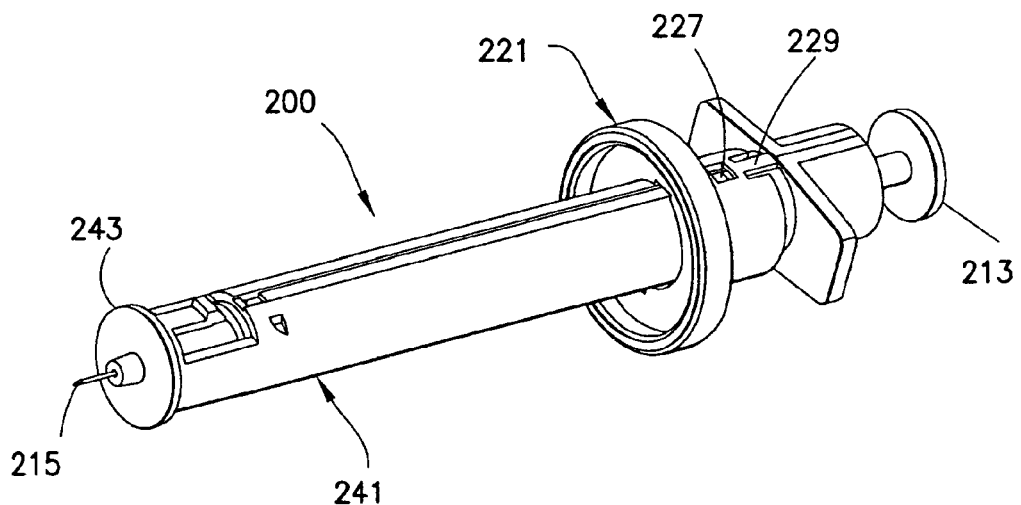
FIG. 3 is a perspective view of the needle adjusting member disposed on the syringe of FIG. 1 in a first position.
Figure 4:
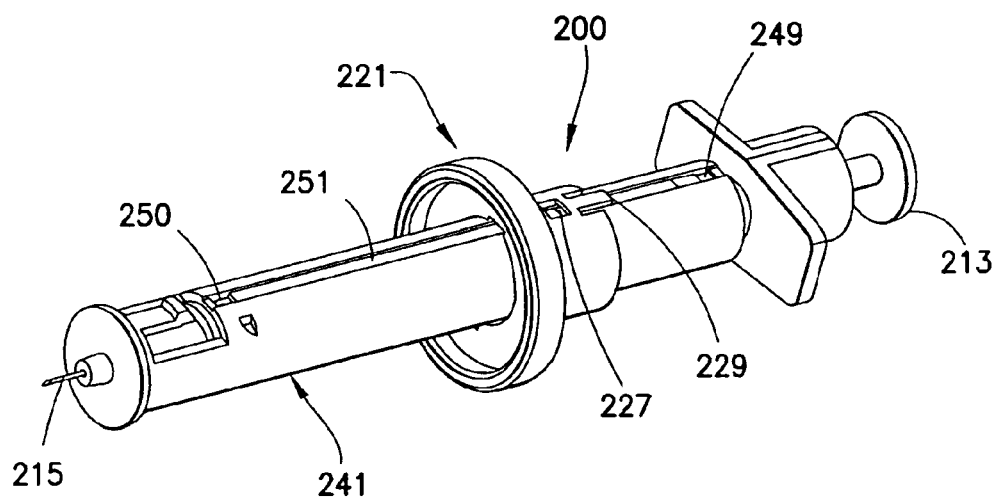
FIG. 4 is a perspective view of the needle adjusting member being moved on the syringe of FIG. 1.

An outer cover 241 is disposed on the syringe body 217 such that the needle adjusting member 221 is movably disposed on the outer cover, as shown in FIGS. 3-5. Preferably, the outer cover 241 is transparent such that the syringe body 217 is visible therethrough. A flange 243 has an opening 244 therein through which the needle 215 passes when the outer cover 241 is disposed on the syringe 211. A wall 245 extends upwardly from the flange 243 and forms a passageway 246 that extends from an end 247 of the wall 245 to the flange 243. The passageway 246 is aligned with the opening 244 to allow the needle 215 to pass therethrough. A first pair of diametrically opposed openings 249 are formed in the wall 245 proximal the end 247 of the wall. A second pair of diametrically opposed openings 250 are formed in the wall 245 proximal the flange 243. An axial groove 251 is disposed in the wall 245 extending from each of the first openings 249 to the second opening 250. A pair of diametrically opposed flexible arms 253 are formed in the wall 245 proximal the flange 243. A hook 254 is formed at the end of the flexible arm 253. Tabs 257 extend inwardly from an inner surface of the outer cover 241. The tabs 257 have a rearward facing ramp 259 (FIG. 6) to allow the tabs to pass over the syringe flange 219 and to prevent the outer cover 241 from being pulled back over the syringe flange 219.

Figure 6:
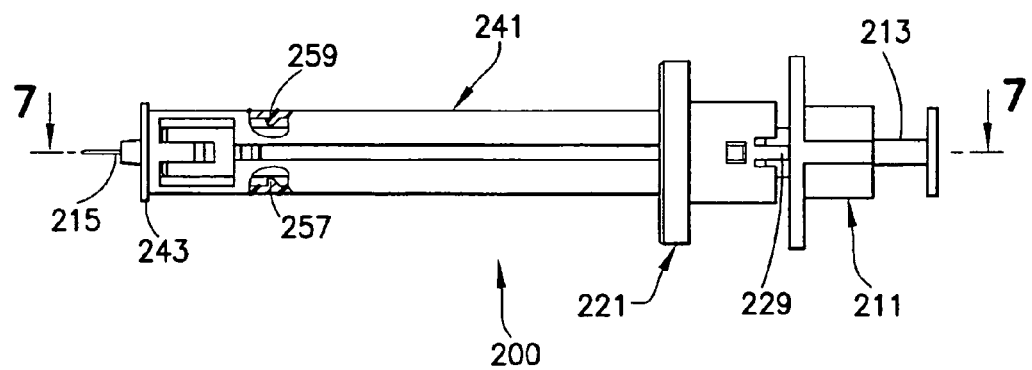
FIG. 6 is an elevational view of the syringe assembly of FIG. 3.

The needle adjusting member 221 is disposed on the outer cover 241 such that the flexible arms 229 are disposed in the grooves 251. The outer cover 241 is then disposed on the syringe body 217 such that the needle 215 extends from the opening 244 in the flange 243. The needle adjusting member 221 is moved on the outer cover 241 toward the plunger 213. Movement of the needle adjusting member 221 is guided by the flexible arms 229 received in the grooves 251. The rearwardly facing ramped portions 259 of the tabs 257 allows the outer cover 241 to pass over the syringe flange 219. The needle adjusting member 221 is moved until the hooks on the flexible arms are received in the first openings 249 and engage the collar 218 of the syringe 211, thereby substantially preventing movement of the needle adjusting member. In this first position of the needle adjusting member 221, as shown in FIGS. 3, 6 and 7, the needle 215 has a first length adapted to withdraw medication from a container, such as a vial.

To prepare the syringe assembly 200 to intradermally inject the medication drawn into the syringe body 217, the flexible arms 229 are removed from the first openings 249 and the syringe collar 218, such that the needle adjusting member 221 and the outer cover 241 are movable rearwardly along the syringe body 217, as shown in FIG. 4. The hooks of the flexible arms 229 are guided by the grooves 251 toward the second openings 250. As the needle adjusting member 221 approaches the flange 243, the notches 230 in the base 223 allow the needle adjusting member to pass over the hooks 254 of the flexible arms 253 of the outer cover.

When the needle adjusting member 221 is in the second position, as shown in FIGS. 5, 8 and 9, the hooks 254 of flexible arms 253 are received by the openings 227 in the wall 226, thereby creating a snap-fit. The flat portions 260 of the tabs 257 abut the syringe flange 219, thereby preventing further rearward movement of the outer cover 241. The rearward movement of the outer cover 241, as shown in FIGS. 7 and 9, shortens the effective length of the needle 215. The flexible arms 229 of the needle adjusting member 221 pass over the syringe flange 219 and are received in the second openings 250 in the outer cover 241, thereby creating a snap-fit and preventing further movement of the needle adjusting member 221. The hooks 235 of the flexible arms 229 abut the syringe flange 219, thereby preventing movement of the needle adjusting member 221 toward the plunger 213. A lower surface 231 of the base 223 of the needle adjusting member 221 is substantially flush with a lower surface 255 of the flange 243. When the needle adjusting member 221 is in the second position the effective length of the needle 215 is shortened, thereby providing a needle length suitable for an intradermal injection.

As shown in FIG. 9, the space 233 within the base 223 of the needle adjusting member 221 allows for growth of a wheal (or bubble) of skin during the injection.

Figure 10:
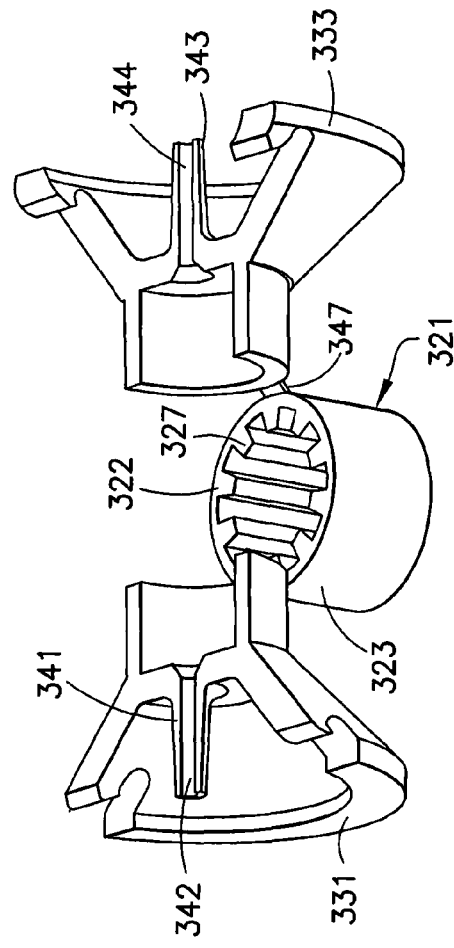
FIG. 10 is a perspective view of a needle adjusting member according to a second exemplary embodiment of the present invention.
Figure 11:
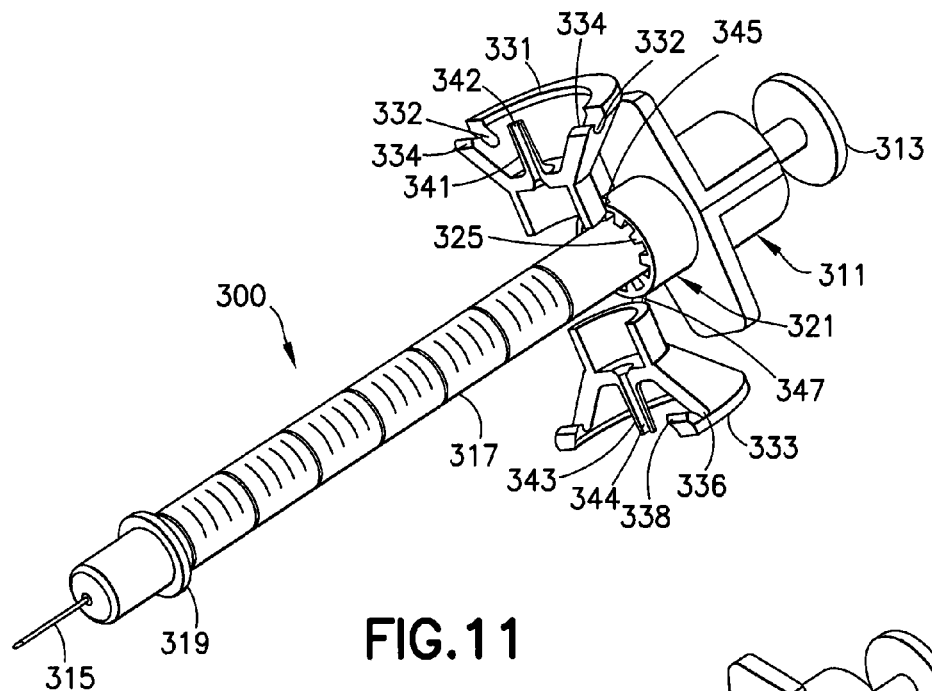
FIG. 11 is a perspective view of the needle adjusting member of FIG. 10 disposed in a first position on a syringe.
Figure 12:
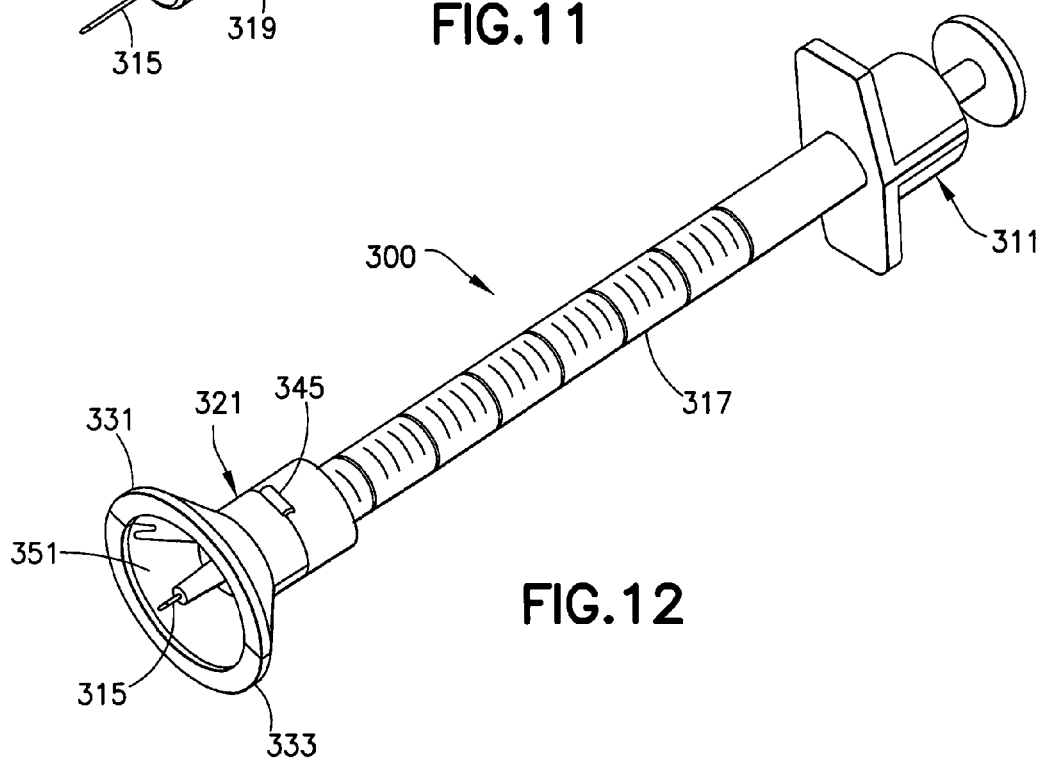
FIG. 12 is a perspective view of the needle adjusting member of FIG. 10 disposed in a second position on a syringe.

In a second exemplary embodiment of the present invention, as shown in FIGS. 10-12, a needle adjusting member 321 has a base 323 having an opening 325 therein for receiving the syringe body 317. First and second housing portions 331 and 333 are pivotally connected to the base 323. Preferably, the first and second housing portions 331 and 333 are connected to the base 323 by first and second hinges 345 and 347. In a pre-use state, as shown in FIG. 10, the first and second housing portions 331 and 333 are open to allow easy access to fill the syringe 311 in a normal manner. Preferably, the needle adjusting member 321 is disposed proximal the plunger 313 to provide better visibility during filling, thereby facilitating filling the syringe. A plurality of teeth 327 extend inwardly from the base 323 to create an interference fit with the syringe body 317, thereby preventing movement of the needle adjusting member 321 in the first position.

After the syringe 311 has been filled, the needle adjusting member 321 is moved rearwardly along the syringe body 317 until a circumferential rib 322 disposed in the opening 325 abuts the syringe flange 319, thereby preventing further movement of the needle adjusting member 321. The plurality of teeth 327 flex to allow the teeth to pass over the syringe flange 319, thereby capturing the syringe flange between the plurality of teeth and the circumferential rib 322. The first and second housing portions 331 and 333 are snapped together around the needle 315 and the base of the syringe 321, as shown in FIG. 12, thereby creating the needle geometry, i.e., a needle 315 having a shorter effective length, to facilitate an intradermal medication injection.

The first housing portion 331 has a pair of grooves 332 and a pair of tabs 334. The second housing portion 333 has a pair of grooves 336 and a pair of tabs 338. The grooves 332 of the first housing portion 331 receive the tabs 338 of the second housing portion 333 and the grooves 336 of the second housing portion 333 receive the tabs 334 of the first housing portion 331 when the first and second housing portions are connected together, as shown in FIG. 12.

The first housing portion 331 has a first projection 341 having a first groove 342 therein. The second housing portion 333 has a second projection 343 having a second groove 344 therein. When the first and second housing portions are connected, as shown in FIG. 12, the first and second projections 341 and 343 abut one another such that the first and second grooves 342 and 344 form a passageway in the needle adjusting member 321 for receiving the needle 315.

A space 351 is formed by the connected first and second housing portions 331 and 333 to provide an area for a skin bubble (wheal) to grow as a result of the injection. Additionally, a wide platform is created by the connected first and second housing portions 331 and 333 to stabilize the syringe assembly 300 during an injection.

As shown in FIGS. 10-12, the needle adjusting member 321 is preferably manufactured as a one-piece molding. Preferably, the needle adjusting member 321 is injection molded.

Figure 13:
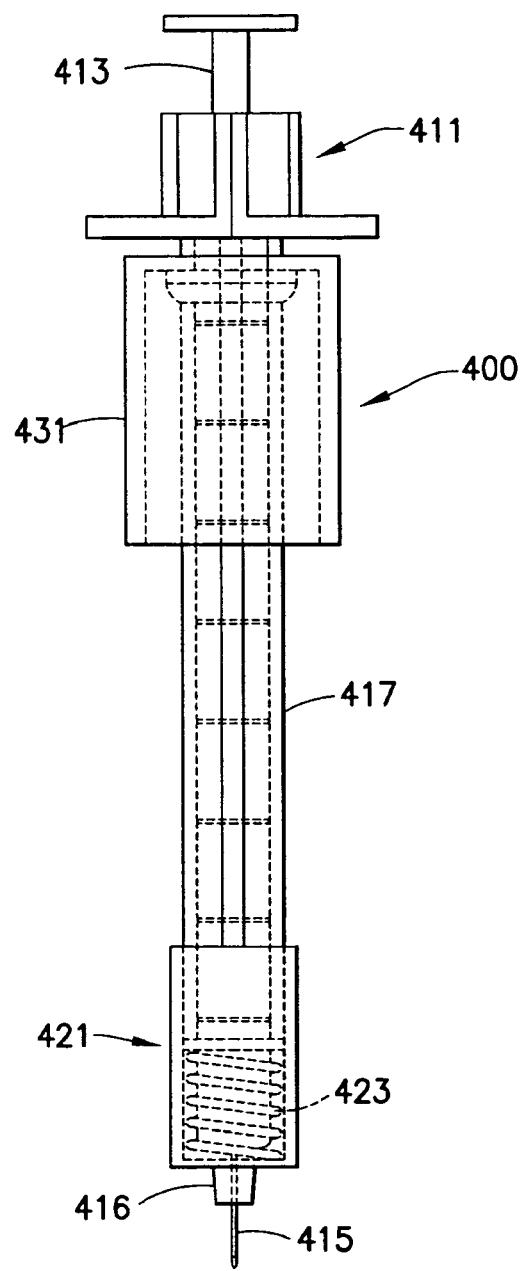
FIG. 13 is a front elevational view of a needle adjusting member disposed on a syringe according to a third exemplary embodiment.

In a third exemplary embodiment of the present invention shown in FIGS. 13-15, a syringe assembly 400 is provided. A conventional insulin syringe 411 having a spring-loaded platform 421 at the base of the needle 415 has a clear needle adjusting member 321 that has a first position proximal the syringe plunger 413, as shown in FIGS. 13 and 14. In this position, the syringe assembly 400 has a longer exposed needle length that allows for normal vial-based syringe filling. After drug filling and priming, the user slides the needle adjusting member 431 down the syringe body 417 to the tip and secures the needle adjusting member in a second position, as shown in FIG. 15, thereby creating the intradermal stand-off and geometry necessary for an intradermal medication injection. While the needle adjusting member 431 is being secured in the second position, the spring-loaded platform 421 is released that slides down the needle and creates an effective short intradermal needle length, such as approximately 1.65 mm.

The spring-loaded platform 421 may be locked forward or allowed to move rearwardly. In the non-locked configuration, the platform 421 is allowed to move back if it contacts a forming wheal and does not constrain the wheal formation as in the fixed or locked configuration.

A light compression spring 423 is assembled and compressed between the nose 416 and the syringe body 417, as shown in FIG. 13. In the pre-use state (FIGS. 13 and 14), the needle length exposed is long enough to allow normal vial filling. Preferably, the exposed needle length for vial filling is at least approximately 5 mm. When the needle adjusting member 431 is slid forward after filling the syringe 411, a simple lever or snap releases the nose 416 from the syringe body 417 and the compression spring 423 pushes the nose forward to shorten the needle 415, as shown in FIG. 15. At substantially the same time, the needle adjusting member 431 is continued to be pushed or slid until the needle adjusting member 431 is secured, such as by snapping, in place, thereby creating the geometry to hold the needle at the correct depth and stabilizing the syringe assembly 400 on the skin surface. The nose 416 is now in a forward position to shorten the needle 415 to an intradermal length. The needle 415 is maintained stationary and in the intradermal layer while the nose 416 is pushed rearwardly to expose more of the needle. By having a fixed needle 415 and allowing for rearward movement of the nose 416 relieves the pressure build-up and helps reduce forces and leakage at the injection site.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A syringe, comprising:
a syringe body for receiving and administering a medicament;
a needle received by said syringe body;
a needle adjusting member movably disposed on said syringe body between first and second positions, such that when said needle adjusting member is in said first position said needle has a first length adapted to draw medicament into the syringe body, and when said needle adjusting member is in said second position said needle has a second length for injecting the medicament, and a space being formed in a lower surface of said needle adjusting member to receive skin during an injection; and
an outer cover disposed on said syringe body such that said needle adjusting member is movably disposed on said outer cover, wherein said outer cover has a first opening at a first end and a second opening at a second end,
wherein said needle adjusting member has a flexible arm engageable with said first opening when said needle adjusting member is in said first position and with said second opening when said needle adjusting member is in said second position, and wherein said needle adjusting member has an opening and said outer cover has a flexible arm at said second end engageable with said needle adjusting member opening when said needle adjusting member is in said second position.

2. The syringe according to claim 1, wherein said outer cover is transparent for viewing said syringe body.

3. The syringe according to claim 1, wherein
an axial groove is disposed in said outer cover and extends between said outer cover first and second openings,
said needle adjusting member flexible arm being received by said axial groove when said needle adjusting member moves between said first and second positions.

4. The syringe according to claim 1, wherein
said needle adjusting member has a base having an opening therein for receiving said syringe body and
first and second housing portions pivotally connected to said base.

5. The syringe according to claim 4, wherein said base has a plurality of teeth extending into said opening to create an interference fit with said syringe body.

6. The syringe according to claim 4, wherein
said first housing portion is separated from said second housing portion when said needle adjusting member is in said first position, and
said first housing portion is connected to said second housing portion when said needle adjusting member is in said second position.

7. The syringe according to claim 6, wherein
said first housing portion has a groove and said second housing portion has a tab,
said groove receiving said tab when said first housing portion is connected to said second housing portion.

8. The syringe according to claim 1, wherein said second needle length is adapted for an intradermal injection.

9. A needle adjusting member for use with a syringe, said needle adjusting member comprising:
a base having an opening for receiving a syringe body, said base being movable on said syringe body between a first position in which a syringe needle has a first length, and a second position in which the syringe needle has a second length, the second length being shorter than said first length to facilitate an injection, and a space being formed in a lower surface of said base to receive skin during an injection; and
an outer cover disposed on said syringe body such that said needle adjusting member is movably disposed on said outer cover, wherein said outer cover has a first opening at a first end and a second opening at a second end,
wherein said needle adjusting member has a flexible arm engageable with said first opening when said needle adjusting member is in said first position and with said second opening when said needle adjusting member is in said second position, and
wherein said needle adjusting member has an opening and said outer cover has a flexible arm at said second end engageable with said needle adjusting member opening when said needle adjusting member is in said second position.

10. The needle adjusting member according to claim 9, wherein
an axial groove is disposed in said outer cover and extends between said outer cover first and second openings,
said needle adjusting member flexible arm being received by said axial groove when said needle adjusting member moves between said first and second positions.

11. The needle adjusting member according to claim 9, further comprising:
first and second housing portions pivotally connected to said base; and
a plurality of teeth extending into said opening to create an interference fit with said syringe body.

12. The needle adjusting member according to claim 11, wherein
said first housing portion is separated from said second housing portion when said needle adjusting member is in said first position, and
said first housing portion is connected to said second housing portion when said needle adjusting member is in said second position.

13. The needle adjusting member according to claim 12, wherein
said first housing portion has a groove and said second housing portion has a tab,
said groove receiving said tab when said first housing portion is connected to said second housing portion.

14. The needle adjusting member according to claim 9, wherein said second needle length is adapted for an intradermal injection.

15. A syringe, comprising:
a syringe body for receiving and administering a medicament;
a needle received by said syringe body; and
a needle adjusting member having an opening and being movably disposed on said syringe body between first and second positions, such that when said needle adjusting member is in said first position said needle has a first length adapted to draw medicament into the syringe body, and when said needle adjusting member is in said second position said needle has a second length for injecting the medicament; and
an outer cover is disposed on said syringe body such that said needle adjusting member is movably disposed on said outer cover, said outer cover having a first opening at a first end and a second opening at a second end; and
wherein said needle adjusting member has a flexible arm engageable with said first opening when said needle adjusting member is in said first position and with said second opening when said needle adjusting member is in said second position, and
said outer cover has a flexible arm at said second end engageable with said needle adjusting member opening when said needle adjusting member is in said second position.

16. A needle adjusting member for use with a syringe, said needle adjusting member comprising:
a base having a first opening for receiving a syringe body, said base being movable on said syringe body between a first position in which a syringe needle has a first length, and a second position in which the syringe needle has a second length, the second length being shorter than said first length to facilitate an injection; and
an outer cover disposed on said syringe body such that said needle adjusting member is movably disposed on said outer cover, said outer cover having a first opening at a first end and a second opening at a second end;
wherein said needle adjusting member has a flexible arm engageable with said first opening when said needle adjusting member is in said first position and with said second opening when said needle adjusting member is in said second position, wherein said needle adjusting member has a second opening and said outer cover has a flexible arm at said second end engageable with said needle adjusting member second opening when said needle adjusting member is in said second position.

\* \* \* \* \*